United States Patent [19]

Del Mar et al.

[11] Patent Number: 5,037,553

[45] Date of Patent: Aug. 6, 1991

[54] ORGANIC CONTAMINANT SEPARATOR

[75] Inventors: Peter Del Mar; Barbara J. Hemberger, both of Los Alamos, N. Mex.

[73] Assignee: The United States of America as represented by the United States Department of Energy, Washington, D.C.

[21] Appl. No.: 418,613

[22] Filed: Oct. 10, 1989

[51] Int. Cl.$^5$ ............................................. B01D 15/08
[52] U.S. Cl. ................................. 210/635; 210/656; 210/198.2; 210/502.1; 55/67; 436/161
[58] Field of Search ................... 210/635, 656, 198.2, 210/692, 502.1; 55/67, 197, 386; 436/161, 162; 422/70; 73/61.1 C

[56] References Cited

U.S. PATENT DOCUMENTS

| | | | |
|---|---|---|---|
| 3,146,192 | 8/1964 | McClintock | 210/40 |
| 3,147,216 | 9/1964 | Oemier et al. | 210/40 |
| 3,668,118 | 6/1972 | Rhodes | 210/30 |
| 3,852,490 | 12/1974 | Kohn | 426/271 |
| 3,966,597 | 6/1976 | Omori et al. | 210/39 |
| 4,042,498 | 8/1977 | Kennedy | 210/26 |
| 4,276,179 | 6/1981 | Seohngen | 210/679 |
| 4,826,603 | 5/1989 | Hayes | 210/635 |
| 4,828,996 | 5/1989 | Seigal | 210/635 |
| 4,836,928 | 6/1989 | Aoyagi | 210/635 |
| 4,872,979 | 10/1989 | Golay | 210/635 |

OTHER PUBLICATIONS

Test methods for Evaluating Solid Wastes, Physical/Chemical Methods, SW-846, U.S. Environment Protection Agency, Office of Solid Waste and Emergency Response, 3rd Edition, District of Columbia (1987), pp. (Abstract-1), (3510-1-3510-7), (3520-1-3520-7), and (8080-1-8080-27).

H. C. Chow et al., "Polyethylene Powder as a Stationary Phase for Preparative-Scale Reversed-Phase High-Performance Liquid Chromatography," Depart. of Chem., Univ. of Calif., vol. 151, No. 3, pp. 357-362 (1978), Journal of Chromatography.

Primary Examiner—Ernest G. Therkorn
Attorney, Agent, or Firm—Bruce H. Cottrell; Paul D. Gaetjens; William R. Moser

[57] ABSTRACT

A process of sample preparation prior to analysis for the concentration of an organic contaminant in an aqueous medium by (a) passing an initial aqueous medium including a minor amount of the organic contaminant through a polyolefin tube having an internal diameter of from about 0.01 to about 2.0 millimeters and being of sufficient length to permit the organic contaminant to adhere to the tube, (b) passing a solvent through the tube, said solvent capable of separating the adhered organic contaminant from the tube.

Further, a chromatographic apparatus for sample preparation prior to analysis for the concentration of an organic contaminant in an aqueous medium, said apparatus including a polyolefin tube having an internal diameter of from about 0.01 to about 2.0 millimeters and being of sufficient length to permit an organic contaminant contained within an aqueous medium passed therethrough to adhere to the tube is disclosed.

8 Claims, 2 Drawing Sheets

ORGANIC CONTAMINANT SEPARATOR

FIELD OF THE INVENTION

The present invention relates generally to the field of analytical chemistry and more particularly to a sample preparation apparatus and technique preceding a standard analysis, i.e., gas or liquid chromatography for determining the concentration of organic contaminants in an aqueous sample. This invention is the result of a contract with the Department of Energy (Contract No. W-7405-ENG-36).

BACKGROUND OF THE INVENTION

Organic contaminants, e.g., certain halogenated organic compounds and polyaromatic hydrocarbons, can find their way into the environment through industrial operations and through the use of pesticides. While many of these compounds have been banned or restricted due to potential health hazards, their presence continues in soil and water samples.

Analysis of water and/or soil samples for halogenated organic compounds has traditionally been conducted by addition of an immiscible solvent, e.g., chloroform, to a water sample whereby the halogenated organic compounds will concentrate in the organic phase, i.e., the immiscible solvent (see Test Methods for Evaluating Solid Wastes, Physical/Chemical Methods, SW-846, U.S. Environmental Protection Agency, Office of Solid Waste and Emergency Response, 3rd edition, Dist. of Columbia (1987) describing an EPA approved method, i.e., method 8080 for Organochlorine Pesticides and PCB's wherein aqueous extractions are conducted by either method 3510—Separatory Funnel Liquid-Liquid Extraction or method 3520—Continuous Liquid-Liquid Extraction, each method requiring large amounts of solvents and considerable time). The solvent phase is then separated from the aqueous phase, the majority of the solvent evaporated off and the halogenated organic compound residue analyzed by standard techniques.

Several repetitions of such an organic phase separation process are generally necessary thereby resulting in the use of a significant volume of solvent. Drawbacks to this traditional organic phase separation process include that it is time-consuming, is often rather imprecise and inaccurate, and presents a further environmental problem by the use and potential for release of chlorinated solvent into the atmosphere as the solvent is removed prior to analysis.

Another analytical technique referred to as solid phase extraction has also been used for separation of organic compounds from aqueous samples. This method uses silica particles coated with selected organic molecules, e.g., polyalkylenimino alkyl polyalkoxy silanes or carboalkoxyalkyl silanes, such silica particles often referred to as bonded phase silicas. The coated silica particles are packed into a chromatographic column and a water sample is percolated through the packed column. Organic compounds within the water sample are attracted to the surface coating on the silica and thus be separated from the water. The organic compounds can then be separated from the packed bed by flushing with a small amount of solvent. This method uses significantly less solvent than the traditional method. However, drawbacks of solid phase extraction include: the potential for decomposition of the coating on the silica particles under certain conditions, e.g., under wide pH fluctuations; the tendency for clogging of the packed columns due to the small particle size; the tendency of the coated silica particles to adsorb water which must be subsequently removed; and, the potential for interference during subsequent analysis of a water sample due to compounds added to the coated silica particles during their manufacturing process. Thus, techniques other than traditional organic phase separation or solid phase separation are still desirable for sample preparation prior to the analysis of water samples.

It has been known that many organic compounds, especially halogenated organic compounds, are attracted to polyolefin material such as polyethylene and polypropylene. For example, U.S. Pat. No. 4,276,179 discloses removal of halogenated hydrocarbons from aqueous solutions by contact with microporous polyolefinic absorbents. However, there is no disclosure regarding removal of the halogenated hydrocarbons from the microporous polyolefinic absorbents or determination of halogenated hydrocarbon concentrations in the initial aqueous sample.

One object of this invention to provide an apparatus and process for sample preparation prior to a standard analysis for organic contaminants, e.g., halogen-containing hydrocarbons, in a water sample.

A further object of this invention to provide an apparatus and process for sample preparation prior to a standard analysis for organic contaminants, e.g., halogen-containing hydrocarbons, in a water sample wherein the sample preparation does not require substantial quantities of solvent in separating the organic contaminants.

Yet another object of this invention to provide an apparatus for sample preparation prior to a standard analysis for organic contaminants, e.g., halogen-containing hydrocarbons, in a water sample wherein the apparatus is substantially free of clogging problems and does not undergo the retention of water.

A still further object of this invention to provide an apparatus and process for sample preparation prior to a standard analysis for organic contaminants, e.g., halogen-containing hydrocarbons, in a water sample wherein the sample preparation provides cleaner extracts in a quicker process and the apparatus can be reused rather than discarded as are the presently available solid phase extraction materials.

SUMMARY OF THE INVENTION

To achieve the foregoing and other objects, and in accordance with the purposes of the present invention, as embodied and broadly described herein, the present invention provides a process of sample preparation prior to analysis for the concentration of an organic contaminant in an aqueous medium comprising: passing an initial aqueous medium including a minor amount of the organic contaminant through a polyolefin tube having an internal diameter of from about 0.01 to about 2.0 millimeters and being of sufficient length to permit the organic contaminant to adhere to the tube; and, passing a solvent through the tube, said solvent capable of removing the adhered organic contaminant from the tube.

The present invention further provides a chromatographic apparatus for sample preparation prior to analysis for the concentration of an organic contaminant in an aqueous medium comprising: a polyolefin tube having an internal diameter of from about 0.01 to about 2.0 millimeters and being of sufficient length to permit an organic contaminant contained within an aqueous medium passed therethrough to adhere to the tube; and, a means of passing through said tube both a first predetermined amount of an aqueous medium containing an organic contaminant at a predetermined rate and a second predetermined amount of a solvent capable of separating the adhered organic contaminant from said tube.

DETAILED DESCRIPTION

Figure 1:
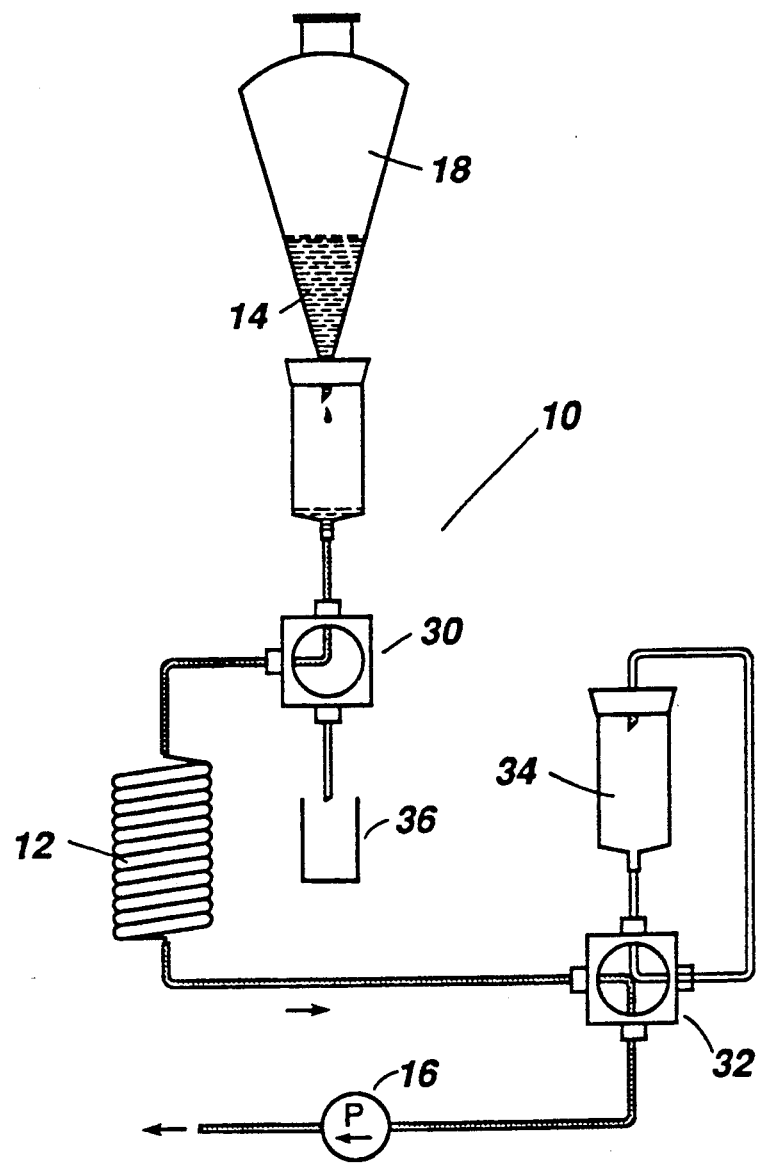
FIG. 1(a) is a schematic drawing of the chromatographic apparatus of the present invention during the separation stage.
FIG. 1(b) is a schematic drawing of the chromatographic apparatus of the present invention during the removal or elution stage.
Figure 1:
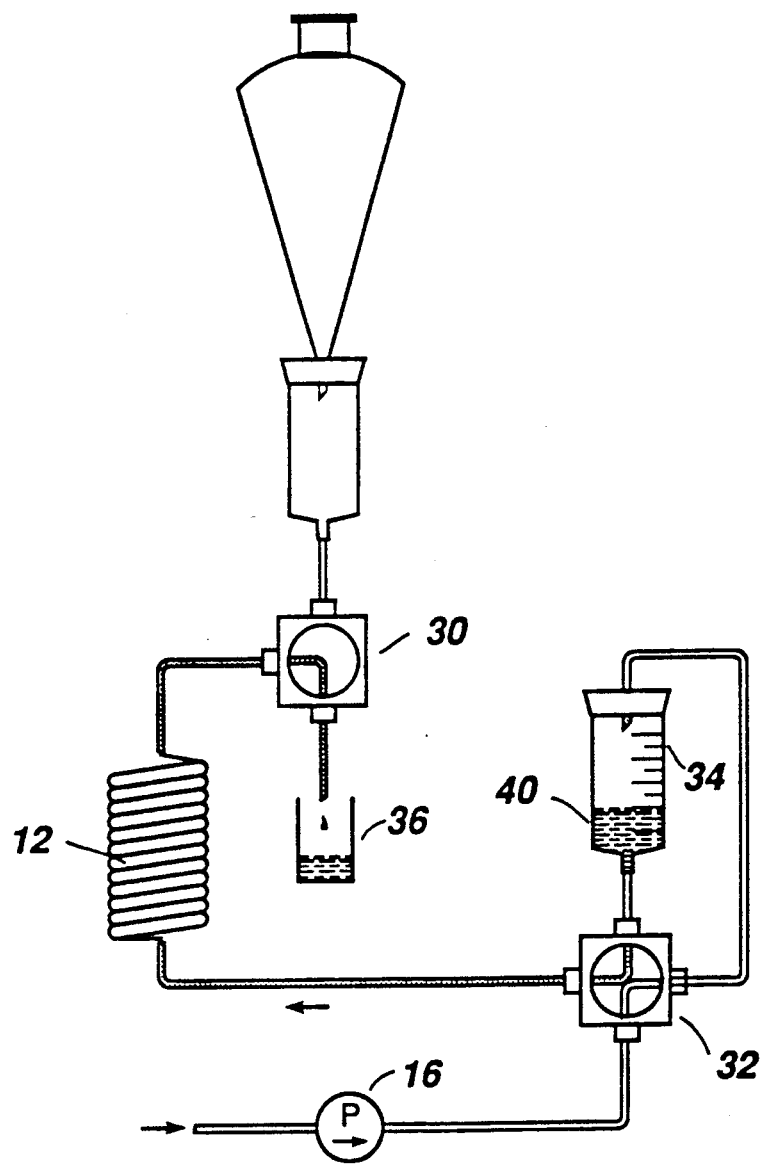

The present invention concerns a chromatographic apparatus for and a process of sample preparation prior to measuring or determining the concentration of organic contaminants, especially halogen-containing hydrocarbons or polyaromatic hydrocarbons, in an aqueous medium. It has now been found that certain organic contaminants can be separated from an aqueous medium by passing the aqueous medium through a column or tube of polyolefin, the tube having a sufficient diameter and length so that organic contaminants can be separated from the aqueous medium by adhering to the tube material. Subsequently, the organic contaminants can be removed or separated from the tube or column by passing a solvent through the tube whereby the concentration of the organic contaminants in the initial aqueous medium can be readily determined.

Polymers from olefinic materials have a high affinity for organic contaminants such as the halogen-containing hydrocarbons described herein. It is the affinity of such olefinic materials for the halogen-containing hydrocarbons and the ability to subsequently separate the halogen-containing hydrocarbons from the olefinic materials, i.e., the polyolefinic column or tube, thus facilitating the present process and apparatus for measurement of the organic contaminant concentrations in the aqueous samples. Suitable polyolefinic materials may include polyethylene, polypropylene, poly-3-methyl butene-1, poly-4-methyl pentene-1, as well as copolymers of propylene, 3-methyl butene-1, 4-methyl pentene-1, or ethylene with each other or minor amounts of other olefins, e.g., copolymers of propylene and ethylene, copolymers of a major amount of 3-methyl butene-1 and a minor amount or a straight chain alkene such as n-octene-1, n-hexadecene-1, n-octadecene-1 or other similar long chain alkenes as well as copolymers of 3-methyl pentene-1 and any of the previously mentioned straight chain alkenes. The preferred polyolefins are polyethylene and polypropylene with polyethylene being most preferred.

Preferably, the polyolefin tubing should not contain additives that interfere with the subsequent analysis for the organic contaminants. Polyolefin tubing can typically include various plasticizers, flexibilizers, anti-oxidants, anti-static agents and the like for use in other applications. Selection of a polyolefin tubing with a minimum of additives simplifies the subsequent analysis.

The column or tube, through which the organic contaminant-containing water sample is passed, should have its internal diameter minimized to increase the contact between the water sample and the tube walls. The lower limit for the internal diameter is limited only by the ability to form such a tube or column and by a need to avoid plugging of the tube or column by any particulates in the water sample. Generally, the internal diameter of the tube will be from about 0.01 to about 2.0 millimeters, preferably from about 0.3 to about 1.0 millimeters. The tube or column in the present invention is devoid of any packing material as such packing material presents the potential for clogging. The use of unfilled tubing alleviates any possible clogging so long as the internal diameter of the tubing is greater than any particles in the aqueous medium.

The length of the column or tube should be of sufficient length to permit organic contaminants in the initial water sample to contact and adhere to the inner wall of the tubing. Generally, with water samples of about 100 to about 500 milliliters (ml) in size and typical organic contaminant concentrations of from about 0.01 to about 10.0 or more micrograms per liter, tube lengths of from about 5 to about 15 feet are sufficient. Variations in tube length can easily be adjusted for different sample sizes, concentrations and internal tubing diameters.

The water sample can be contacted with the tube at any convenient temperature, e.g., from about 10° Centigrade (C.) to about 50° C., or pressure, e.g., superatmospheric, subatmospheric or atmospheric.

Higher temperatures are not generally preferred as the solubilities of the organic contaminants in the aqueous samples can be affected. The most convenient temperature is generally ambient temperature and the most convenient pressure is generally atmospheric.

After the water sample is passed through the column or tube to separate organic contaminants from the water, a suitable solvent can be passed through the column or tube to separate the adhered organic contaminants from the tube. Typically, as little as 10 ml of solvent is needed flush or separate the organic contaminants from the tubing. This is substantially less solvent than necessary in previous analytical techniques for such organic contaminants and is one of the major advantages of the present process and apparatus. Suitable solvents include hexane, iso-octane, acetone, acetonitrile, and lower alcohols, e.g., methanol, ethanol, propanol and butanol. Preferred solvents include hexane and iso-octane.

In the process of the present invention, the water sample is passed through the column or tube at flow rates of from about 0.6 to about 2.0 ml/minute, preferably from about 0.8 to about 1.2 ml/minute. The water sample may be passed through the tube by gravity flow but the flow rate is preferably controlled by a pump, e.g., a peristaltic pump.

FIGS. 1(a) and 1(b) show schematic drawings of the chromatographic apparatus used for sample preparation of an aqueous medium containing an organic contaminant, FIG. 1(a) in the separation stage and FIG. 1(b) in the removal or elution stage. Apparatus 10 includes as a principal component a polyolefin tube 12 having an internal diameter of from about 0.01 to about 2.0 millimeters and tube 12 being of sufficient length to permit an organic contaminant contained within an aqueous sample 14 passed therethrough to adhere to the tube. The apparatus further includes a means of passing a predetermined amount of aqueous sample 14 containing an organic contaminant through tube 12 at a predetermined rate, and of passing a predetermined amount of a solvent 40 capable of removing or separating the adhered organic contaminant from tube 12 through the tube.

The means of passing a predetermined amount of an aqueous medium containing an organic contaminant through the tube at a predetermined rate can include a pump 16 attached to an outflow end of the tube whereby the flow rate of the aqueous medium through the tube can be controlled. Optionally, the apparatus may further include a holding vessel 18 wherein the aqueous medium is held prior to processing.

The means of passing a predetermined amount of solvent 40 through tube 12 can include a second holding vessel 34 wherein solvent 40 is held prior to the flushing of the tube. Alternatively, solvent 40 can be entered into tube 12 from the same holding vessel as the initial aqueous medium 14 as long as proper rinsing precautions are taken to avoid inadvertent contamination of the solvent.

Apparatus 10 can further include a means of collecting said predetermined amount of solvent after passage through said tube. Such collection means can be a vessel 36 of sufficient size to contain the flushed solvent.

Apparatus 10 can still further include a first valve means 30 and a second valve means 32 whereby the flow of the liquids through apparatus 10 is controlled.

Calculation of the concentration of organic contaminants in the predetermined amount of aqueous medium can be accomplished by first concentrating the final solvent elute containing the organic contaminants removed from the aqueous sample by evaporating off most of the solvent and then injecting the organic contaminant-containing solvent into a gas chromatograph equipped with a suitable detector such as an electron capture detector or a flame ionization detector. Such techniques are well known to those skilled in the art of analytical chemistry.

The halogen-containing hydrocarbons which may be removed from aqueous media include aliphatic, cycloaliphatic, and heterocyclic halogen-containing hydrocarbons containing from about 1 to about 30 carbon atoms, aromatic halogen-containing hydrocarbons and their derivatives such as alkyl-substituted aromatic halogen-containing hydrocarbons having from about 6 to about 30 carbon atoms. Such aromatic halogen-containing hydrocarbons are typically employed as pesticides.

Representative examples of chlorine-containing hydrocarbons include N-(trichloromethylthio)phthalimide (Phalton fungicide); 1,2,3,3,10,10-hexachloro-1,4,4a,5,8,8a-hexahydro-1,4,5,8-endo-dimethanonaphthalene (aldrin); 1,2,3,4,10,10-hexachloro-6,7-epoxy-1,4,4a,5,6,7,8,8a-octahydro-1,4-endo-exo-5,8-dimethanonaphthalene (diendrin); 1,2,3,4,10,10-hexachloro-6,7-epoxy-1,4,4a,5,6,7,8,8a-octahydro-1,4-endo-endo-5,8-dimethanonaphthalene (endrin); dichlorodiphenyldichloroethylene (DDE); dichlorodiphenyldichloroethane (DDD); 1,1,1-trichloro-2,2-bis(chlorophenyl)ethane (DDT); 1,4,5,6,7,8,8-heptachloro-3a,4,7,7a-tetrahydro-4,7-methanoindene (heptachlor); octachloro-4,7-methanotetrahydroindane (chlordane); N-trichloromethylthio- or N-tetrachloromethylthio-substituted (haloalkylsulfenylated) carboximides such as cis-N-(trichloromethylthio)-4-cyclohexene-1,2-dicarboximide (Captan(TM)); N-(1,1,2,2-tetrachloroethylthio)-4-cyclohexene-1,2-dicarboximide (Difolatan(TM) fungicide); gamma-benzene hexachloride (lindane); toxaphene; methoxychlor; hexachlorocyclopentadiene; carbon tetrachloride; trichloroethylene; trichloromethane; ethylene dichloride; and vinyl chloride.

Other representative examples of halogen-containing hydrocarbons and their derivatives include polychlorinated biphenyls, such as the Arochlor(TM) series of compounds made by Monsanto Co. Specific common chlorobiphenyl compounds include 2-chlorobiphenyl; 3-chlorobiphenyl; 4-chlorobiphenyl; 2,2'-dichlorobiphenyl; 3,3'-dichlorobiphenyl; 4,4'-dichlorobiphenyl; 3,5-dichlorobiphenyl; 2,5-dichlorobiphenyl; 3,4-dichlorobiphenyl; 2,3-dichlorobiphenyl; 2,4'-dichlorobiphenyl; 2,4,5-trichlorobiphenyl; 2,3,5-trichlorobiphenyl; 2,4,4'-trichlorobiphenyl; 2,5,4'-trichlorobiphenyl; 3,5,4'-trichlorobiphenyl; 3,4,2'-trichlorobiphenyl; 3,5,2'-trichlorobiphenyl; 3,4,3',4'-tetrachlorobiphenyl; 3,4,2',5'-tetrachlorobiphenyl; 2,6,2',6'-tetrachlorobiphenyl; 2,5,3',5'-tetrachlorobiphenyl; 2,4,2',4'-tetrachlorobiphenyl; 2,5,2',5'-tetrachlorobiphenyl; 2,4,5,3',4'-pentachlorobiphenyl; 3,4,5,3',4',5,-hexachlorobiphenyl; 2,4,6,2',4',6'-hexachlorobiphenyl; 2,3,5,6,2',3',5',6'-octachlorobiphenyl; and 2,3,4,5,6,2',3',4',5',6'-decachlorobiphenyl.

Polyaromatic hydrocarbons may also be separated from aqueous samples by the present process and apparatus. Among the polyaromatic hydrocarbons which may be separated are included naphthalene, substituted naphthalenes, anthracene, substituted anthracenes and the like.

The present invention is more particularly described in the following example which is intended as illustrative only, since numerous modifications and variations will be apparent to those skilled in the art.

EXAMPLE 1

Four sample aliquots of water were each spiked with an equal portion of a known pesticide sample. The pesticide sample was prepared from a sealed ampule supplied by the Environmental Protection Agency (EPA) for EPA's Performance Evaluation Study WPO-22 and had known pesticide levels. The EPA sample included the following pesticides: aldrin, dieldrin, DDD, DDE, DDT, heptachlor, and heptachlor epoxide. The sample preparation apparatus included a ten foot column of polyethylene tubing having an internal diameter of 1/16 inch (available as bev-a-line(TM) lined tubing from U.S. Plastics Corp., Lima, Ohio) and a pump at a setting sufficient to pump the liquid sample through the tubing at a flow rate of about 0.83 ml/min. A spiked water sample was pumped through the tubing. After the water sample was passed through the tubing, about 9 ml of hexane was passed through the tubing at a rate of about 2 ml/min. The hexane elute was then passed through a one inch column of sodium sulfate to remove any residual water. An additional one half milliliter of hexane was passed through the drying column to rinse any residual elute. The solvent (hexane) extract was evaporated down to a one ml volume under dry nitrogen, spiked with 40.0 microliters of an internal standard mix containing four brominated biphenyls in iso-octane, and analyzed in a HP-5880 gas chromatograph (available from the Hewlett-Packard Co.) with an electron capture detector. The process was repeated for each of the four samples. The time for completion of each sample was about three hours.

An additional set of four sample aliquots of water were each spiked with an equal portion of a known pesticide sample and run through the sample preparation apparatus to determine the recovery percentage, i.e., the percentage of each known pesticide actually recovered from the water samples.

The average results of the four sample runs analyzed by the gas chromatograph are shown in Table 1 in comparison to the known EPA values.

TABLE 1

| Pesticide | recovery of pesticide from solution percentage | Measured Average Value from Example 1 in micrograms/liter | EPA value in micrograms/liter | EPA accepted range in micrograms/liter |
|---|---|---|---|---|
| aldrin | 55% | 0.617 | 0.647 | 0.170–0.873 |
| dieldrin | 78% | 0.525 | 0.546 | 0.300–0.720 |
| DDD | 66% | 0.858 | 0.949 | 0.439–1.31 |
| DDE | 52% | 0.662 | 0.656 | 0.297–0.912 |
| DDT | 65% | 0.859 | 0.825 | 0.370–1.16 |
| heptachlor | 76% | 0.791 | 0.833 | 0.326–1.11 |
| heptachlor epoxide | 73% | 0.576 | 0.586 | 0.332–0.777 |

A comparison of the values obtained in Example 1 with the reported EPA values shows the accuracy and precision that can be obtained with the present apparatus and process with the use of significantly less solvent than either the present separatory funnel liquid-liquid extaction process or continuous liquid-liquid extraction process. In addition, the present apparatus and process allows sample preparation to be completed in substantially less time and with substantially less solvent than the present EPA approved separatory funnel liquid-liquid extraction.

Although the present invention has been described with reference to specific details, it is not intended that such details should be regarded as limitations upon the scope of the invention, except as and to the extent that they are included in the accompanying claims.

What is claimed is:

1. A process of sample preparation and analysis of an organic contaminant in an aqueous medium comprising:
    a. passing an initial aqueous medium including a minor amount of the organic contaminant through a polyolefin tube having an internal diameter of from about 0.01 to about 2.0 millimeters and being of sufficient length to permit the organic contaminant to adhere to the tube;
    b. passing a solvent through the tube, said solvent capable of removing the adhered organic contaminant from the tube; and
    c. chromatographically analyzing said contaminant.

2. The process of claim 1 wherein said organic contaminant is selected from the group consisting of aliphatic, cycloaliphatic, heterocyclic, aromatic, and alkyl-substituted aromatic hydrocarbons having from 1 to about 30 carbon atoms.

3. The process of claim 1 wherein the polyolefin tube is comprised of either polyethylene or polypropylene.

4. The process of claim 3 wherein the internal diameter of the tube is from about 0.3 to about 1.0 millimeter.

5. The process of claim 4 wherein the solvent is selected from the group consisting of hexane, iso-octane, acetone, acetonitrile, or a lower alcohol.

6. The process of claim 4 wherein the solvent is hexane.

7. The process of claim 1 wherein the internal diameter of the tube is from about 0.3 to about 1.0 millimeter.

8. The process of claim 1 wherein the solvent is selected from the group consisting of hexane, iso-octane, acetone, acetonitrile, or a lower alcohol.

* * * * *